(12) United States Patent
Camponovo et al.

(10) Patent No.: US 7,691,871 B2
(45) Date of Patent: Apr. 6, 2010

(54) MULTIVITAMIN SYRUP FOR CHILDREN OR YOUNG ADULTS

(75) Inventors: Fabrizio Camponovo, Pedrinate (CH); Fabio Danini, Vignone (IT)

(73) Assignee: Boehringer Ingelheim International GmbH, Ingelheim (DE)

( * ) Notice: Subject to any disclaimer, the term of this patent is extended or adjusted under 35 U.S.C. 154(b) by 0 days.

(21) Appl. No.: 10/918,990

(22) Filed: Aug. 16, 2004

(65) Prior Publication Data

US 2005/0095262 A1 May 5, 2005

(30) Foreign Application Priority Data

Aug. 19, 2003 (EP) ................. 03018606

(51) Int. Cl.
| | |
|---|---|
| *A61K 31/51* | (2006.01) |
| *A61K 31/525* | (2006.01) |
| *A61K 31/44* | (2006.01) |
| *A61K 31/195* | (2006.01) |
| *A61K 31/16* | (2006.01) |
| *A61K 31/675* | (2006.01) |
| *A61K 31/593* | (2006.01) |
| *A61K 31/355* | (2006.01) |
| *A61K 31/19* | (2006.01) |
| *A61K 31/13* | (2006.01) |

(52) U.S. Cl. ............... 514/276; 514/89; 514/167; 514/168; 514/251; 514/345; 514/356; 514/357; 514/458; 514/557; 514/563; 514/564; 514/565; 514/629; 514/665; 514/904

(58) Field of Classification Search .............. 514/276
See application file for complete search history.

(56) References Cited

U.S. PATENT DOCUMENTS

| | | | |
|---|---|---|---|
| 5,388,690 A | 2/1995 | Mutterle et al. | |
| 5,474,209 A | 12/1995 | Vallet Mas et al. | |
| 5,750,142 A * | 5/1998 | Friedman et al. | 424/450 |
| 5,770,215 A * | 6/1998 | Moshyedi | 424/440 |
| 5,965,162 A * | 10/1999 | Fuisz et al. | 424/464 |
| 6,245,803 B1 | 6/2001 | Acosta et al. | |
| 6,475,539 B1 * | 11/2002 | DeWille et al. | 426/72 |
| 2003/0099722 A1 | 5/2003 | Baxter | |

FOREIGN PATENT DOCUMENTS

| | | |
|---|---|---|
| CA | 2 500 282 A1 | 4/2004 |
| DE | 20116346 U1 * | 12/2001 |
| DE | 102 45 172 A1 | 4/2004 |
| EP | 0 093 090 A2 | 2/1983 |
| EP | 0 344 849 A2 | 6/1989 |
| EP | 0 599 189 A2 | 1/1994 |
| EP | 0 577 200 A1 | 5/1994 |
| RO | 76070 A * | 5/1983 |
| WO | WO 03/035027 A1 | 5/2003 |

OTHER PUBLICATIONS

Food and Nutrition Board, Commission on Life Sciences, National Research Council; Recommended Dietary Allowances, 10th Edition; (c) 1998; National Academy Press, Washington, DC; Chapter 6: Protein and Amino Acids, pp. 52-76.*
XP-002265768, Multi-vitamin syrup for children—contg. thiamine hydrochloride, riboflavin, pyridoxine hydrochloride, ascorbic acid and nicotinamide in aromatised liq. vehicle.
H. Bohles, et al. "Reflections about possible nutritional supplements in infant milk formula" Zeitschrift Fuer Ernaehrungswissenschaft, Steinkopf Verlag, Darmstadt, Germany, vol. 37, No. 2, 1998, pp. 132-146—XP000981644.
Anthony T. Diplock; Antioxidant Nutrients and Disease Prevention: An Overview; American Journal Clinical Nutrition (1991) vol. 53 pp. 189S-193S.
George G. Graham et al; Lysine Enrichment of Wheat Flour: Evaluation in Infants; the American Journal of Clinical Nutrition (1969) vol. 22, No. 11 pp. 1459-1468.
Anthony A. Albanese et al; Lysine Supplementation in Infant Feeding Dosage Considerations; NY State Journal of Medicine ( 1955) vol. 55 pp. 3453-3456.
Robert Civitelli et al; Dietary 1-Lysine and Calcium Metabolism in Humans; Nutrition (1992) vol. 8, No. 6 pp. 400-405.
Peter Furst; Dietary 1-Lysine Supplementation: A Promising Nutritional Tool in the Prophylaxis and Treatment of Osteoporosis; Nutrition (1993) vol. 9, No. 1 pp. 71-72.
Nestor W. Flodin; the Metabolic roles, Pharmacology, and Toxicology of Lysine; Journal of American College of Nutrition (1997) vol. 16, No. 1 pp. 7-21.
International Search Report for PCT/EP2004/009121 mailed on Oct. 25, 2004.
Documenta Geigy Scientific Tablets, 457-497, (Diem and Cemtuer eds., 7th ed., 1975).

* cited by examiner

*Primary Examiner*—Johann R Richter
*Assistant Examiner*—Nathan W Schlientz
(74) *Attorney, Agent, or Firm*—Michael P. Morris; David A. Dow; Edouard G. Lebel

(57) ABSTRACT

The invention relates to an improved pharmaceutical or dietary composition in form of an aqueous syrup, consisting essentially of (a) vitamins recommended for consumption by children or young adults, (b) a suitable calcium source, (c) at least one dibasic amino acids, (d) taurine, (e) at least one solubilizer, (f) at least one additional agent selected from the group consisting of sweetening agents, flavoring agents, flavor enhancers, preservatives, antioxidants, co-solvents, and (g) water.

9 Claims, No Drawings

MULTIVITAMIN SYRUP FOR CHILDREN OR YOUNG ADULTS

RELATED APPLICATIONS

This Application claims benefit to EP 03018606, filed Aug. 19, 2003 the contents of which are incorporated herin by reference.

BACKGROUND OF THE INVENTION

1. Technical Field

The invention relates to an improved pharmaceutical or dietary composition in form of an aqueous syrup, consisting essentially of (a) vitamins recommended for consumption by children or young adults, (b) a suitable calcium source, (c) at least one dibasic amino acid, (d) taurine, (e) at least one solubilizer, (f) at least one additional agent selected from the group consisting of sweetening agents, flavoring agents, flavor enhancers, preservatives, antioxidants, co-solvents, and (g) water.

2. Background Information

Vitamin and mineral preparations are commonly administered to treat specific medical conditions or as general nutritional supplements. Recent studies have elucidated the important physiological roles played by vitamins and minerals, and established a correlation between deficiencies or excesses of these nutrients and the etiologies of certain disease states in humans. See, e.g., Diplock, "Antioxidant Nutrients and Disease Prevention: An Overview," Am. J. Clin. Nutr., 53:189-193 (1991); Documenta Geigy Scientific Tables, 457-497, (Diem and Cemtuer eds., 7th ed., 1975).

It has further become recognized that various, groups of the human population require different quantities and types of vitamins and minerals to prevent or alleviate diseases, as well as to maintain general good health. For example, it is known that lysine as an essential amino acid enhances appetite and, together with Vitamin D3, improves the absorption of calcium. The prior art dealing with lysine as nutritional supplement may be best illustrated by the following references:

Albanese A. A. et al., NY State J. Med. 1955; 55, 3453-3456 describe lysine supplementation in infant feeding. Graham G. G. et al., Am. J. Clin. Nutr. 1969; 22 (11), 1459-1468 describe the effect of lysine enrichment of wheat flour for the evaluation in infants. Civitelli R. et al., Nutrition 1992; 8 (6), 400-405, disclose the metabolism of (L)-lysine and calcium in humans. Fürst P., Nutrition 1993; 9 (1), 71-72 suggests (L)-lysine as a nutritional tool in the prophylaxis and treatment of osteoporosis. Flodin N. W., J. Am. Coll. Nutr. 1997; 16 (1), 7-21, reviews the metabolic roles, the pharmacology and the toxicology of lysine.

The International patent application WO 03/035027, for example, discloses a chewable tablet for children comprising a multivitamin composition, lysine and a taste masking agent.

The Russian patent RU 2 189 753 suggests a sterilized milk product for infant nutrition from birthday to five months comprising milk, whey protein concentrate, oils, sugar, minerals, water-soluble vitamins, fat-soluble vitamins, inositol, L-carnitine, taurine and water.

The German utility model DE 201 16 346 U1 discloses a micronutrient combination product based on vitamins, folic acid, magnesium, arginine, coenzyme Q1O, carotenoids and omega fatty acids. However, this document clearly states, that those components have a low miscibility and that it is difficult to obtain homogenous compositions, in particular in aqueous solutions, since some of the components might partly or completely become insoluble or have a low resorbtion in the body. Accordingly, DE 201 16 346 U1 suggests to divide the different active ingredients into different dosage forms. Despite the foregoing efforts to improve vitamin, mineral and amino acid supplementation, in particular for children, conventional supplements exhibit several deficiencies. One notable problem is that due to the bad miscibility and the comparably high amount of different vitamins the dosage forms become very voluminous and hard to swallow especially for children.

Problems, thus, arise concerning the compliance of children for taking different dosage forms, in order to have a complete coverage of their needs regarding micronutrients.

Accordingly, there is a need to provide humans, in particular children and/or juveniles with supplementation of essential amino acids and vitamins.

Moreover, the vitamin and mineral preparations available up to now for children do not provide sufficient active ingredients to improve appetite and growth.

It would therefore be desirable to provide a multi-vitamin and mineral supplement for children which overcomes the aforementioned deficiencies of the prior art.

BRIEF SUMMARY OF THE INVENTION

Surprisingly, it has been found that a pharmaceutical or dietary composition in form of an aqueous syrup, consisting essentially of (a) vitamins recommended for consumption by children or young adults, (b) a calcium source, (c) at least one dibasic amino acid selected from arginin and lysine, (d) taurine, (e) at least one solubilizer, (f) at least one additional agent selected from the group consisting of sweetening agents, flavoring agents, flavor enhancers, preservatives, antioxidants, co-solvents, and (g) water, is an optimal micronutrient for children, it is highly stable and provides a good compliance by children.

Another aspect of the present invention is a method of supplementing the dietary needs of a child or a young adult, said method comprising administering to said child or young adult a dietary supplementing amount of the pharmaceutical or dietary unit dosage form according to the invention.

Furthermore, the invention relates to the use of a pharmaceutical or dietary unit dosage form according to the invention, for the preparation of a pharmaceutical or dietary composition for supplementing the dietary needs of a child or young adult.

Furthermore, the invention relates to a pharmaceutical kit of parts for the preparation of a pharmaceutical or dietary unit dosage form according to any one of claims 1 to 9 comprising two compartments (I) and (II), wherein compartment (I) contains:

(a) vitamins recommended for consumption by children or young adults, (b) a calcium source, (c) at least one dibasic amino acid, (d) taurine, (e) at least one solubilizer, and (f) at least one additional agent selected from the group consisting of sweetening agents, flavoring agents, flavor enhancers, preservatives, antioxidants, co-solvents; and compartment (II) contains:

(g) water and optionally liquid components of (e) and (f).

DETAILED DESCRIPTION OF THE INVENTION

The components (a) to (d) are formulated with the components (e) to (g) together in one stable formulation. The formulation is in the form of a stable aqueous syrup for oral administration.

The term "a person" or "a person in need thereof" or "patient" as used hereinabove and hereinbelow relates to a healthy female or male child or young adult who is in need for an improvement of his or her nutritional status. As a rule such persons are young people with an age of between 10 months and 20 years, preferably between 1 and 15 years having an mean age of 8 years.

The term "effective amount" as used herein means an amount sufficient to improve the nutritional status when components (a) to (d) are administered together in one single dosage form. As a rule the combination of the components (a) to (d) shows a synergistic effect, which means that the effect on the nutritional status is higher than expected from the mere additive effects of the single components (a) to (d) and/or the single components (a), (b), (c) and (d) alone.

Under the term "vitamin recommended for consumption by children or young adults" is understood vitamins which are beneficial for young people.

A wide variety of vitamins (a) are safe for consumption by children These vitamins include, for example, Vitamin A or beta-carotene, Vitamin $B_1$ (as Thiamin or Thiamin mononitrate), Vitamin $B_2$ (as Riboflavin), Vitamin $B_3$ (as Niacin), Vitamin $B_6$ (as Pyridoxine or Pyridoxine hydrochloride), Vitamin $B_9$ (Folic Acid), Vitamin $B_{12}$ (cyanocobalamine or hydroxycobalamine), Vitamin H (Biotin), Vitamin C (Ascorbic Acid), Vitamin D, Vitamin E (as dl-Alpha Acetate), Vitamin K, Dexpanthenol, Nicotinamide (Niacinamide), Tocopheryl, and mixtures thereof. Such vitamins are commercially available from sources known by those of skill in the art, such as Hoffmann-LaRoche Inc. (Nutley, N.J.).

Preferably the dosage form according to the invention contains at least one vitamin selected from the group consisting of β-carotene, Vitamin $B_1$, Vitamin $B_2$, Vitamin $B_6$, Vitamin $B_{12}$, Vitamin C, Vitamin $D_3$, Vitamin E, Folic Acid, Dexpanthenol, Nicotinamide and Biotin, in particular such dosage forms, in which the multivitamin mixture consists of Vitamin $B_1$, Vitamin $B_2$, Vitamin $B_6$, Vitamin $D_3$, Vitamin E, Dexpanthenol and Nicotinamide.

Furthermore the preferred calcium source (b) is selected from calcium lactate and calcium carbonate, most preferred is calcium lactate.

Preferably the dibasic amino acids (c) is a mixture of arginin and lysine.

Arginine is known as a semi-essential amino acid, as it is usually synthesised in the human body but in amounts not sufficient to cover the needs of young, growing subjects. Arginine has demonstrated effects on endocrine function and is known to stimulate the release of catecholamines, insulin, glucagon, prolactin, and growth hormone. It is also the precursor of nitric oxide (NO) and many of arginine's clinical actions are thought to be mediated by its effect on endothelial-derived relaxing factor.

Supplemental arginine is apparently able to up-regulate the immune function and plays an important role of arginine in immunonutrition (defined as the effect of the provision of specific nutrients on the immune function). Arginine is seen as a promising therapeutic factor in paediatric care, being the substrate for NO-synthase, as NO plays an essential role in smooth muscle relaxation and blood flow. Specifically, some authors foresee a clear role of this amino acid in the prevention and treatment of respiratory problems, along with the already mentioned activity in the immune system. Clinical applications of arginine are wide ranging. This amino acid, for instance, has been described to benefit individuals with reduced immune defences. Because of arginine's NO-stimulating effects, this amino acid has also been reported to be useful in the prevention and treatment of cardiovascular diseases.

Lysine is necessary for the endogenous synthesis of carnitine, which is provided exogenously by milk and meat, two dietary components often missing in the developing countries. Carnitine is essential for the transport of long-chain fatty acids through the mitochondrial membrane. In the mitochondria Beta-oxidation of fatty acids takes place, thus providing energy during fasting periods or during extended physical exercising. Clinical signs of carnitine deficiency are, e.g., muscular weakness, hypotonia and intestinal dysmotility. Rice, wheat, millet, oats and rye contain extremely low doses of lysine. For population groups having cereals as their main source of proteins, a dietary supplement of lysine is recommended. This is particularly true for infants and children of pre-school age, because their lysine requirement can not be adequately covered otherwise. Lysine has been confirmed to be the limiting amino acid in the diet of children in pre-school and school age. In such cases, the amino acid imbalance can lead to malnutrition. While an amino acid imbalance is unlikely in healthy populations of industrialised countries, this is by no means a rare occurrence in other parts of the world. A number of studies have shown that the use of lysine as a supplement in the diet of children living mainly off cereals resulted in an accelerated weight gain. Lysine was confirmed to be the limiting amino acid in rice and wheat and the usefulness of a dietary supplement of lysine to these two cereals has now been demonstrated. Recently, the potential usefulness of lysine for both preventive and therapeutic interventions in osteoporosis has been discussed. A clinical study has suggested that L-lysine can both enhance intestinal calcium absorption and at the same time improve the renal conservation of the absorbed calcium. Thus, dietary L-lysine supplementation appears to be a promising nutritional tool in the prophylactic treatment of osteoporosis.

Taurine (2-aminoethanesulfonic acid) is a so-called conditionally-essential amino acid. It is found free or in simple peptides but is not utilised in protein synthesis. In vivo studies have shown that taurine is essential in a number of aspects of mammalian development. In addition, low levels of taurine are associated with various pathological lesions, including cardiomyopathy, retinal degeneration, and growth retardation. Taurine is known to play an important role in numerous physiological functions, including detoxification, membrane stabilisation, osmoregulation, and modulation of cellular calcium levels. Taurine has also been used in the treatment of cardiovascular diseases, epilepsy and other seizure disorders, macular degeneration, Alzheimer's disease, hepatic disorders, and cystic fibrosis. Recent research has shown that taurine plays a protective role against oxidant-induced damage in the limphocytes, without, however, being directly an antioxidant. Human-based studies have recently provided valuable information on the potential therapeutic applications of taurine in immune and homeostatic functions, a feature that was previously based only on animal studies. As for most amino acids occurring naturally in the human body, the evidence used to show the importance of taurine in nutrition is mostly linked to epidemiological evidence. Taurine is important in central nervous system development and a dietary supplementation in infancy and in later stages is a recommended step in preventive nutrition. It has been also demonstrated that taurine is involved in the modulation of apoptosis in several cell types. Therefore, a quite important role of taurine in a protection of the immune system can at least be postulated. Beneficial effects of taurine have been shown in a number of indications, including congestive heart failure and cystic fibrosis.

There is a need for a hydrophylic/lipophylic balance in order to solubilize the lypophylic ingredients (i.e. Vitamin D, Vitamin E and the flavouring agent). It has been found that certain solubilizers (e) are suitable to solubilize these lipophilic components in the aqueous syrup according to the invention. The substances used as solubilizer are usually interface-active surfactants. These surfactants are amphiphilic (bifunctional) compounds with at least one hydrophobic and one hydrophilic part of the molecule. The hydrophobic group is usually a polyether hydrocarbon chain, in particular a polyethyleneoxy chain, if possible a straight chain, with eight to 22 carbon atoms. Particular solubilizers may also have (dimethyl)-siloxane chains or perfluorinated hydrocarbon chains as the hydrophobic part of the molecule. The hydrophilic group is either a negatively or positively charged (hydratable) or a neutral polar head group. Of the solubilizers, nonionic solubilizers are preferred, particularly preferred are polyalkylene glycols, polyvinyl pyrolidones, polyethylenoxy alkoxylates, ethylenoxy/propyleneoxy block co-polymers, polyglucose alkoxylates and polysorbates and analogs thereof, including various copolymers, polymer blends and modified polymers thereof.

Particularly preferred are polysorbates, these are polyoxyethylene sorbitan fatty acid ester such as Tween® 20 or Tween® 80 or mixtures thereof. Most preferably, the solubilizer (e) is a mixture consisting of 20 to 60%, in particular about 40% by weight of polysorbate 80 and 40 to 80%, in particular about 60% by weight of polysorbate 20.

The term "pharmaceutical composition" means a composition, which is suitable for prescription and OTC medicaments, and which are available from doctors, in chemist's shop or in drugstrores, only.

The term "dietary supplement" means a composition, which is for supplementing the regular food intake with additional nutritional elements to enhance quality of life, and which are freely available without prescription in groceries or super market, but not only in drugstores.

Preferably the additional agent (f) comprises at least one sweetening agent, at least one flavoring agent, at least one flavor enhancer, at least one preservative, at least one antioxidant, and at least one co-solvent.

Preferably the sweetening agent is selected from the group consisting of sodium or calcium saccharinate, ammonium cyclamate, ammonium glycirhizinate, Aspartame (N-L-α-aspartyl-L-phenylalanine 1-methylester), glucose and glucitols such as inositol, mannitol, xylitol, sorbitol or dulcitol.

Preferably the flavoring agent is selected from the group consisting of natural citrus or orange or tangerine essence and Prosweet®, which is a commercially available natural flavoring.

Ideally, the antioxidant will be soluble in the syrup and is safe for use in foods and pharmnaceutical preparations. Among the water-soluble materials, ascorbic acid at 0.1 to 1.0 mg/mL was found to reduce oxidative degradation sufficiently.

Moreover, it has been found that the addition of small amounts of an aminopolycarboxylic acid, the term specifically including salts of the acids, can stabilize the syrups against degradation. Useful aminopolycarboxylic acids and salts thereof are those which are safe for ingestion and have sufficient solubility in the syrup formulations to make a stable single phase composition. Commercially available compounds which could be used include iminodiacetic acid, methyliminodiacetic acid, nitrilotriacetic acid, ethylenediaminetetraacetic acid ("EDTA"), diethylenetriaminepentaacetic acid, 1,2-diaminocyclohexane-tetraacetic acid, N-hydroxyethylenediaminetriacetic acid and related compounds. Mixtures of two or more of the foregoing are suitable for use. From the aspects of ready availability, safety, efficacy and cost, the sodium salt of EDTA is presently preferred, and the remainder of this description will focus on those materials.

The composition of the invention may also contain additional ingredients such as cosolvents, including dimethyl isosorbide, oils, including soybean oil, and alcohols such as ethanol. The cosolvent may comprise from 0% by weight to about 2% by weight of the composition of the invention, and more preferably from about 0.0005% by weight to about 0.5% by weight of the solution of the invention. Most preferably, the cosolvent is ethanol and comprises from about 0.0005% by weight to about 0.005% by weight of the solution of the invention. Oils may comprise from 0% to about 2% by weight of the solution of the invention, and more preferably from 0% to about 1% by weight of the solution of the invention.

The pH of the composition may be adjusted by the addition of small amounts of inorganic and/or organic acids, in particular phosphoric acid and/or citric acid, usually no more than about 1-2% by weight of the composition.

In particular, the additional agent (f) essentially consists of sorbitol, saccharin sodium, orange essence, phosphoric acid, citric acid, potassium sorbate, sodium benzoate, disodium edetate, (L)-ascorbic acid and ethanol.

In a preferred embodiment the composition according to the invention consists essentially of:
(a) Vitamin $B_1$, Vitamin $B_2$, Vitamin $B_6$, Vitamin $D_3$, Vitamin E, Dexpanthenol and Nicotinamide;
(b) calcium lactate;
(c) arginin and (L)-lysine hydrochloride;
(d) taurine;
(e) at least one polysorbate;
(f) sorbitol, saccharin sodium, orange essence, phosphoric acid, citric acid, potassium sorbate, sodium benzoate, disodium edetate, (L)-ascorbic acid and ethanol; and
(g) water.

Most preferably 1 ml of the pharmaceutical composition or dietary supplement consists essentially of:
(a) 0.1 to 0.3 mg of Vitamin $B_1$, 0.1 to 0.3 mg of Vitamin $B_2$, 0.2 to 0.6 mg of Vitamin $B_6$, 10 to 40 I.U. of Vitamin $D_3$, 0.5 to 1.5 mg of Vitamin E, 0.2 to 1.0 mg of Dexpanthenol and 0.7 to 2.0 mg of Nicotinamide;
(b) 20 to 150 mg of calcium lactate;
(c) 5 to 15 mg of arginin and 10 to 30 mg of (L)-lysine hydrochloride;
(d) 5 to 15 mg of taurine;
(e) 3.0 to 25 mg of at least one polysorbate;
(f) 200 to 300 mg of sorbitol (non-crystallizable) 70% solution, 0.5 to 1.5 mg of saccharin sodium, 0.5 to 1.5 mg of orange essence, 10 to 20 mg of phosphoric acid (concentrate 85%), 0.2 to 1.5 mg of citric acid monohydrate, 0.5 to 1.5 mg of potassium sorbate, 0.8 to 2.0 mg of sodium benzoate, 0.05 to 0.5 mg of disodium edetate, 0.5 to 1.5 mg of (L)-ascorbic acid and 0.001 to 0.1 mg of ethanol; and
(g) water.

The components should remain in solution to achieve the benefits of the invention, and the solution should remain stable over time and under conditions normally encountered in consumer applications. The solution disclosed in the present invention has been found stable and robust in a number of tests. For instance, the solution has been placed "on the shelf" at room temperature for extended periods of time, and has remained clear and stable, without precipitation of the active ingredients. Moreover, the solution has been subjected to alternating refrigeration and room temperature conditions, and the active ingredients have not crystallized, and have remained stable and clear.

The solution of the invention may be prepared through mixing of the ingredients. This mixing takes place preferably at an elevated temperature and with applied shear. While the applied shear does not necessarily allow for greater solubility of any ingredient, it appears to provide better stability of the solution during handling and storage. Preferably, a mixture of the active ingredients and the excipients is then added to water. The process may be carried out in whole or in part in a nitrogen atmosphere if the presence of oxygen might discolor or otherwise damage any ingredient in the solution.

The kit of parts, as a rule, will consist of a bottle containing water (g) and optionally the other liquid excipients such as the cosolvent, and a bottle cap comprising a containment which represents a housing for the active ingredients (a) to (d) and the solid components of the excipients (e) and (f). Before opening the bottle, the components contained in the bottle cap are released and admixed with the liquid components contained in the body of the bottle. Such bottles are disclosed for example by the European patent applications EP 0 093 090, EP 0 344 849, EP 0 577 200 and EP 0 599 189 and the German patent application DE 102 45 172.9, the complete disclosure of which is hereby incorporated by reference.

The Example that follows serves to illustrate the formulation according to the invention. It is intended solely as possible procedure described by way of example, without restricting the invention to its content.

EXAMPLE 1

A multivitamin syrup is prepared with the following components:

| Components | Declared amount (mg/ml) | Function |
|---|---|---|
| Active ingredients | | |
| Calcium Lactate $5H_2O$ | 66.66 mg | active ingredient |
| Corresponding to: | | |
| Calcium | 8.67 mg | |
| Thiamine hydrochloride | 0.20 mg | active ingredient |
| Vitamin B1 | | |
| Riboflavin-5'-Na phosphate•$2H_2O$ | 0.23 mg | active ingredient |
| Vitamin B2 | | |
| Pyridoxine hydrochloride | 0.40 mg | active ingredient |
| Vitamin B6 | | |
| Cholecalciferol | 0.67 μg | active ingredient |
| Vitamin D3 | 26.67 IU | |
| d,l-α-Tocopherol acetate | 1.00 mg | active ingredient |
| Nicotinamide | 1.33 mg | active ingredient |
| Vitamin PP | | |
| D-Panthenol | 0.67 mg | active ingredient |
| Dexpanthenol | | |
| Taurin | 10 mg | active ingredient |
| Arginin | 10 mg | active ingredient |
| L-Lysine hydrochloride | 20 mg | active ingredient |
| Excipients | | |
| Orange essence | 1.00 mg | flavoring agent |
| Sorbitol 70% sol. (non crystallizing) | 240.00 mg | solvent, sweetening agent |
| Carboxymethylcellulose sodium (Carmellose sodium) | 6.86 mg | suspending agent |
| Polysorbate 80 | 5.00 mg | solubilizer |
| Polysorbate 20 | 7.50 mg | solubilizer |
| Saccharin sodium salt•$2H_2O$ | 1.00 mg | sweetening agent |
| Phosphoric acid concentrated (85% w/w) | 14.70 mg | acidifier and flavor enhancer |
| Potassium sorbate | 1.18 mg | preservative |
| Sodium benzoate | 1.34 mg | preservative |
| Citric acid•$H_2O$ | 0.67 mg | flavor enhancer |
| Ethylenediaminotetraacetate disodium salt•$2H_2O$ (Disodium edetate) | 0.10 mg | stabilizing agent |
| L-Ascorbic acid | 1.00 mg | antioxidant |
| Ethanol 96% | 0.02 mg | solvent |
| Purified water | q.s. ad 1 ml | solvent |

The active ingredients and the excipients are mixed and dissolved in water.

The invention claimed is:

1. A pharmaceutical or dietary composition in the form of an aqueous syrup, wherein 1 ml thereof consists of:
    (a) 0.1 to 0.3 mg of Vitamin $B_1$, 0.1 to 0.3 mg of Vitamin $B_2$, 0.2 to 0.6 mg of Vitamin $B_6$, 10 to 40 I.U. of Vitamin $D_3$, 0.5 to 1.5 mg of Vitamin E, 0.2 to 1.0 mg of Dexpanthenol and 0.7 to 2.0 mg of Nicotinamide;
    (b) 20 to 150 mg of calcium lactate;
    (c) 5 to 15 mg of arginine and 10 to 30 mg of (L)-lysine hydrochloride;
    (d) 5 to 15 mg of taurine;
    (e) 3.0 to 25 mg of at least one polysorbate;
    (f) 200 to 300 mg of sorbitol (non-crystallizable) 70% solution, 0.5 to 1.5 mg of saccharin sodium, 0.5 to 1.5 mg of orange essence, 10 to 20 mg of phosphoric acid (concentrate 85%), 0.2 to 1.5 mg of citric acid monohydrate, 0.5 to 1.5 mg of potassium sorbate, 0.8 to 2.0 mg of sodium benzoate, 0.05 to 0.5 mg of disodium edetate, 0.5 to 1.5 mg of (L)-ascorbic acid and 0.001 to 0.1 mg of ethanol; and
    (g) water.

2. A method of supplementing the dietary needs of a child or a young adult, said method comprising administering to said child or young adult a dietary supplementing amount of a pharmaceutical or dietary composition form according to claim 1.

3. A ready-to use kit of parts for the preparation of a pharmaceutical or dietary composition comprising two compartments (I) and (II), wherein
    compartment (I) consists of
    (a) Vitamin $B_1$, Vitamin $B_2$, Vitamin $B_6$, Vitamin $D_3$, Vitamin E, Dexpanthenol and Nicotinamide,
    (b) calcium lactate,
    (c) arginine and (L)-lysine hydrochloride,
    (d) taurine,
    (e) at least one polysorbate,
    (f) sorbitol (non-crystallizable), saccharin sodium, orange essence, phosphoric acid, citric acid monohydrate, potassium sorbate, sodium benzoate, disodium edetate, (L)-ascorbic acid and ethanol; and
    compartment (II) consists of (g) water, wherein components (a)-(g) are present in sufficient amounts to prepare the pharmaceutical or dietary composition according to claim 1.

4. A pharmaceutical or dietary composition in the form of an aqueous syrup, wherein 1 ml thereof consists of:

(a) 0.1 to 0.3 mg of Vitamin $B_1$, 0.1 to 0.3 mg of Vitamin $B_2$, 0.2 to 0.6 mg of Vitamin $B_6$, 10 to 40 I.U. of Vitamin $D_3$, 0.5 to 1.5 mg of Vitamin E, 0.2 to 1.0 mg of Dexpanthenol and 0.7 to 2.0 mg of Nicotinamide;
(b) 20 to 150 mg of calcium lactate;
(c) 5 to 15 mg of arginine;
(d) 5 to 15 mg of taurine;
(e) 3.0 to 25 mg of at least one polysorbate;
(f) 200 to 300 mg of sorbitol (non-crystallizable) 70% solution, 0.5 to 1.5 mg of saccharin sodium, 0.5 to 1.5 mg of orange essence, 10 to 20 mg of phosphoric acid (concentrate 85%), 0.2 to 1.5 mg of citric acid monohydrate, 0.5 to 1.5 mg of potassium sorbate, 0.8 to 2.0 mg of sodium benzoate, 0.05 to 0.5 mg of disodium edetate, 0.5 to 1.5 mg of (L)-ascorbic acid and 0.001 to 0.1 mg of ethanol; and
(g) water.

5. A method of supplementing the dietary needs of a child or a young adult, said method comprising administering to said child or young adult a dietary supplementing amount of a pharmaceutical or dietary composition according to claim 4.

6. A ready-to use kit of pans for the preparation of a pharmaceutical or dietary composition comprising two compartments (I) and (II), wherein
compartment (I) consists of
(a) Vitamin $B_1$, Vitamin $B_2$, Vitamin $B_6$, Vitamin $D_3$, Vitamin E, Dexpanthenol and Nicotinamide,
(b) calcium lactate,
(c) arginine,
(d) taurine,
(e) at least one polysorbate,
(f) sorbitol (non-crystallizable), saccharin sodium, orange essence, phosphoric acid, citric acid monohydrate, potassium sorbate, sodium benzoate, disodium edetate, (L)-ascorbic acid and ethanol; and
compartment (II) consists of (g) water, wherein components (a)-(g) are present in sufficient amounts to prepare the pharmaceutical or dietary composition according to claim 4.

7. A pharmaceutical or dietary composition in the form of an aqueous syrup, wherein 1 ml thereof consists of:

(a) 0.1 to 0.3 mg of Vitamin $B_1$, 0.1 to 0.3 mg of Vitamin $B_2$, 0.2 to 0.6 mg of Vitamin $B_6$, 10 to 40 I.U. of Vitamin $D_3$, 0.5 to 1.5 mg of Vitamin E, 0.2 to 1.0 mg of Dexpanthenol and 0.7 to 2.0 mg of Nicotinamide;
(b) 20 to 150 mg of calcium lactate;
(c) 10 to 30 mg of (L)-lysine hydrochloride;
(d) 5 to 15 mg of taurine;
(e) 3.0 to 25 mg of at least one polysorbate;
(f) 200 to 300 mg of sorbitol (non-crystallizable) 70% solution, 0.5 to 1.5 mg of saccharin sodium, 0.5 to 1.5 mg of orange essence, 10 to 20 mg of phosphoric acid (concentrate 85%), 0.2 to 1.5 mg of citric acid monohydrate, 0.5 to 1.5 mg of potassium sorbate, 0.8 to 2.0 mg of sodium benzoate, 0.05 to 0.5 mg of disodium edetate, 0.5 to 1.5 mg of (L)-ascorbic acid and 0.001 to 0.1 mg of ethanol; and
(g) water.

8. A method of supplementing the dietary needs of a child or a young adult, said method comprising administering to said child or young adult a dietary supplementing amount of a pharmaceutical or dietary composition according to claim 7.

9. A ready-to use kit of parts for the preparation of a pharmaceutical or dietary composition comprising two compartments (I) and (II), wherein
compartment (I) consists of
(a) Vitamin $B_1$, Vitamin $B_2$, Vitamin $B_6$, Vitamin $D_3$, Vitamin E, Dexpanthenol and Nicotinamide,
(b) calcium lactate,
(c) (L)-lysine hydrochloride,
(d) taurine,
(e) at least one polysorbate,
(f) sorbitol (non-crystallizable), saccharin sodium, orange essence, phosphoric acid, citric acid monohydrate, potassium sorbate, sodium benzoate, disodium edetate, (L)-ascorbic acid and ethanol; and
compartment (II) consists of (g) water, wherein components (a)-(g) are present in sufficient amounts to prepare the pharmaceutical or dietary composition according to claim 7.

* * * * *